(12) United States Patent
Diaz Offeney et al.

(10) Patent No.: US 10,772,715 B2
(45) Date of Patent: Sep. 15, 2020

(54) INJECTION PISTOL FOR ANIMAL TREATMENT WITH IDENTIFICATION ASSISTANT

(71) Applicant: DIGIRODEO S.A., Buenos Aires (AR)

(72) Inventors: Fernando Oscar Diaz Offeney, Buenos Aires (AR); Carlos Ignacio Iturriaga, Ciudad Autónoma de Buenos Aires (AR); Leopoldo Simini, Ciudad Autónoma de Buenos Aires (AR); Nicolás Alejandro Reyes Viserie, Buenos Aires (AR)

(73) Assignee: DIGIRODEO S.A., Ciudad Autónoma de Buenos Aires (AR)

( * ) Notice: Subject to any disclaimer, the term of this patent is extended or adjusted under 35 U.S.C. 154(b) by 182 days.

(21) Appl. No.: 15/961,501

(22) Filed: Apr. 24, 2018

(65) Prior Publication Data

US 2018/0344442 A1 Dec. 6, 2018

Related U.S. Application Data

(60) Provisional application No. 62/489,882, filed on Apr. 25, 2017.

(51) Int. Cl.
*A61D 7/00* (2006.01)
*H04W 4/80* (2018.01)
(Continued)

(52) U.S. Cl.
CPC ............... *A61D 7/00* (2013.01); *A61D 1/025* (2013.01); *A61M 5/178* (2013.01); *H04W 4/80* (2018.02);
(Continued)

(58) Field of Classification Search
CPC ............ A61D 7/00; A61D 1/02; A61D 1/025; H04W 4/80; H04W 76/10; A61M 5/178; A61M 2005/3125
See application file for complete search history.

(56) References Cited

U.S. PATENT DOCUMENTS 10,130,766 B1 * 11/2018 Bibian ................ A61M 5/1723
2002/0188470 A1 * 12/2002 Hogan .................. G16H 10/60
705/2

(Continued)

*Primary Examiner* — Nathan R Price
*Assistant Examiner* — Jacob Michael Lindsay
(74) *Attorney, Agent, or Firm* — Florek & Endres PLLC (57) ABSTRACT

An injecting gun for the treatment of animals with identification aid with a push button on the handle comprising a body formed by two main housings linked by their edges with delimitate the free space, in which there is an electronic card consisting of: a CPU (Central Processing Unit) which is connected by means of: a) a UART (Universal Asynchronous Receiver/Transmitter) module with connections to: i) a RFID (Radio-Frequency IDentification) module, ii) a wireless connectivity module; and iii) a keyboard; b) a GPIO (General Purpose Input/Output) module with connections to: iii) a plurality of LEDs (Light Emitting Diode), iv) a vibrator, vi) a buzzer, vii) a syringe sensor, viii) a verification sensor, and ix) a TFT (Thin-Film Transistor) liquid crystal parallel port; c) a USB module (Universal Serial Bus) with: x) a micro USB plug (micro USB); wherein, said CPU is connected to a memory; and wherein said CPU is connected to an energy source, which is connected to a charger and energy manager.

15 Claims, 5 Drawing Sheets

(51) Int. Cl.
  *A61D 1/02* (2006.01)
  *A61M 5/178* (2006.01)
  *A61M 5/315* (2006.01)
  *H04W 76/10* (2018.01)
  *A61M 5/31* (2006.01)

(52) U.S. Cl.
  CPC . *A61M 5/31593* (2013.01); *A61M 2005/3125* (2013.01); *A61M 2205/3584* (2013.01); *A61M 2205/502* (2013.01); *H04W 76/10* (2018.02)

(56) References Cited

U.S. PATENT DOCUMENTS

| | | | | |
|---|---|---|---|---|
| 2003/0038721 A1* | 2/2003 | Hogan | A61D 7/00 | 340/573.3 |
| 2003/0043043 A1* | 3/2003 | Hogan | G06F 19/00 | 340/573.3 |
| 2004/0015123 A1* | 1/2004 | Smith | A61M 5/204 | 604/65 |
| 2005/0261633 A1* | 11/2005 | Khalaj | A61M 5/20 | 604/181 |
| 2007/0219480 A1* | 9/2007 | Kamen | A61M 5/16804 | 604/20 |
| 2011/0224613 A1* | 9/2011 | D'Antonio | A61M 5/204 | 604/131 |
| 2013/0141217 A1* | 6/2013 | Goren | A61M 5/20 | 604/181 |
| 2013/0174618 A1* | 7/2013 | Brooks | G07C 9/00309 | 70/91 |
| 2014/0324089 A1* | 10/2014 | Chan | A61M 5/20 | 604/189 |
| 2014/0330215 A1* | 11/2014 | Kikuchi | A61M 5/20 | 604/189 |
| 2015/0248833 A1* | 9/2015 | Arne | G01D 21/00 | 340/870.07 |
| 2015/0290392 A1* | 10/2015 | Henderson | A61M 5/427 | 604/111 |
| 2015/0359968 A1* | 12/2015 | Steel | A61M 5/20 | 604/189 |
| 2016/0038266 A1* | 2/2016 | Edwards | A61D 7/00 | 604/66 |
| 2016/0157524 A1* | 6/2016 | Bowen | A61D 7/00 | 604/66 |
| 2016/0184520 A1* | 6/2016 | Veyrent | A61M 5/2033 | 604/503 |
| 2016/0296313 A1* | 10/2016 | Buckley | A61M 5/1452 | |
| 2016/0324613 A1* | 11/2016 | Halamish | A61D 1/025 | |
| 2017/0017218 A1* | 1/2017 | Hou | H04L 12/2827 | |
| 2017/0340424 A1* | 11/2017 | Edwards | A61D 7/00 | |

* cited by examiner

INJECTION PISTOL FOR ANIMAL TREATMENT WITH IDENTIFICATION ASSISTANT

FIELD OF THE INVENTION

The present invention belongs to the field of veterinary accessories for administering injections, more preferably, it refers to those devices that allow to identify animals, to determine administration dose and to count the administered doses, even more preferably it is related to gun-type syringes that may process, store and transfer information on a treatment and/or be employed as identification aid.

DESCRIPTION OF PRIOR ART

Typically, injections in animals are given with gun syringes where each activation of the trigger corresponds to a dose delivered. These doses are measured in cubic centimeters, and generally, the amount given may be regulated within the range between 1 ml y 5 ml depending on the vaccine or the drug being administered.

In several situations, the amount of administrations is calculated approximately as per the number of vials or bottles of used vaccine or veterinary product or, simply, they are not counted. This is how, typically, once the vaccinated cattle passes through the tube, the work is finished with no registration at al.

Most of syringes currently on the market do not have application counter, as they neither have any kind of identifying device. This way, one may know the exact number of cattle to be vaccinated, but there is no precise information on how many applications were performed by the end of work.

Likewise, there are situations where there is no exact knowledge on the number of animals present in a troop to be treated and the vaccination work is used to count them manually.

Sometimes they are passed from a corral to another one to count them as they pass through a gate or tube, but this management is against the welfare of the animals since it stresses them when making unnecessary non-routine movements.

In order to count the animals of the rodeos at the same time they are vaccinated, a technique was implemented which allows performing both tasks simultaneously without impeding each other. There are devices that allow separating the vaccinator from the work of counting animals, which is a very important complication in huge troops.

These devices are an invaluable tool that allows establishing a control on vaccinated animals which are submitted to official vaccination plans, such as foot and mouth disease or brucellosis. Thus, the official vaccinator will be able, for example, to verify that the informed animals to be vaccinated match the administered doses.

In order to solve this inconvenience, some devices have been proposed that may be coupled to a syringe which can accurately count the number of doses administered thus improving the performance of said element by facilitating, at the same time, the work of vaccinating personnel.

Particularly, patent AR080390B1 refers to a device that, when being coupled to a vaccination syringe, digitally counts the number of administrations performed. A button is pressed when triggering said syringe and a signal is sent to the digital counter, which sums up by 1 (one) unit with a range from 0 to 99999. The main advantage of this complementary product is the accuracy and the control achieved on the quantitative number of doses administered.

However, in spite of the achievement of this device, it is still a need to have a vaccination device that allows reading and recording each animal in different stages of its development from its birth to its slaughter, such as vaccinations, treatment of diseases, weightings, deliveries, etc. This accounting and recording of events are of fundamental importance for traceability of animals.

Therefore, it an object of this invention to provide for a syringe able to accurately record each event happening during the life of each animal when it occurs, being thus able to easily make an individual recording of each one of the animals of a troop by identifying them with different treatments performed and which are necessary for their traceability from birth to slaughter, at the same time facilitating the job of the personnel in charge of its performance.

SUMMARY OF THE INVENTION

It is therefore an object of the present invention to achieve an injecting gun for the treatment of animals with an identification aid having a push button on the handle comprising a body formed by two main housings connected through their edges which delimitate a free space, in which there is an electronic card formed by:
a CPU (Central Processing Unit) which is connected by means of:
  a) a UART (Universal Asynchronous Receiver/Transmitter) module with a multiplicity of connections to:
    i) one RFID module,
    ii) a wireless connectivity module; and
    iii) a keyboard (27);
  b) a GPIO (General Purpose Input/Output) module with a multiplicity of connections to:
    iii) a plurality of LEDs (Light Emitting Diode),
    iv) a vibrator,
    vi) a buzzer,
    vii) a syringe sensor,
    viii) a verification sensor, and
    ix) one parallel port of a TFT (Thin-Film Transistor) liquid crystal screen;
  c) one USB (Universal Serial Bus) module with:
    x) one micro USB plug (micro USB);
  wherein said CPU is connected to a memory; and
  wherein said CPU is connected to a power source, which is connected to a battery charger and energy manager.

Preferably, said CPU is a built-in component and it is selected from Cortex-M0, Cortex-M0+, Cortex-M3, Cortex-M4, Cortex-M7, Cortex-M23, and Cortex-M33

More preferably, the CPU is a built-in component Cortex-M4 204 MHz.

Preferably, the RFID (Radio-Frequency Identification) module is selected from a RFID UHF (Ultra High Frequency) module, a RFID LF (Low Frequency) module, and combinations thereof.

Also preferably, the wireless connectivity module is selected from a BLUETOOTH® wireless networking module, a wireless WiFi module, a ZIGBEE® wireless networking module, a wireless GSM (Global System for Mobile communications) module, and combinations thereof.

Preferably, the identification sensor is selected from tactile switches, Hall effect switches, potentiometer and stepper motor.

When the identification sensor is a tactile switch, then a first switch activates the RFID module which excites an electronic earring, which sends the signal back which is received by the reader antenna at the injecting gun therefore recognizing the datum which is saved in the memory of the injecting gun; and a second switch which is activated when giving an injection and matches the reader reading, confirming that the animal has been injected.

Likewise, the first and second tactile switches are associated with the respective different application volumes, wherein said first and second tactile switches are coordinated with a plurality of additional tactile switches which are associated to different application volumes, and wherein said tactile switches are activated one after the other when the injecting gun trigger is lowered and raised during the performance of each administration.

Accordingly, the first tactile switch is associated to the activation of the RFID module and to an injection volume of 1 ml; the second tactile switch is associated to the validation of administration and to an injection volume of 2 ml; a third tactile switch is associated to an injection volume of 3 ml; a fourth tactile switch is associated to an injection volume of 4 ml; y and a fifth tactile switch is associated to an injection volume of 5 ml.

Operatively, by lowering and raising the trigger of the injecting gun when performing each administration, the RFID module is activated, the volume of each performed administration is identified and the performed administration is validated, these data being saved on the memory associated to the CPU.

Particularly, said memory is selected from a proper internal memory of the CPU, an external memory and a combination thereof.

Particularly preferably, said external memory is an SD memory card (SD card, Secure Digital card).

In a further preferred embodiment, the energy source is at least one Li-Ion (Lithium-Ion) battery or a LiPo (Lithium Polymer) battery, which may be charged by means of a battery charger associated to an energy managing circuit.

Preferably, through the USB module of the CPU the battery is charged from an electromotor source, or information is loaded and downloaded to/from the injecting gun to a peripheral device.

Also preferably, through the BLUETOOTH® wireless networking and/or WiFi and/or ZIGBEE® wireless networking and/or GSM module, information is loaded and downloaded to/from the injecting gun to a peripheral device.

Even more preferably, the peripheral device is chosen from cell phones, tablets, computers, and any other device that supports BLUETOOTH® wireless networking and/or WiFi and/or ZIGBEE® wireless networking and/or GSM connectivity such as scales, identifiers, mechanic fixes, hubs, switches or routers.

Alternatively, by disassembling the section used for injecting animals it is turned into an identification device.

DETAILED DESCRIPTION OF THE INVENTION

It is therefore the object of the present invention to provide for an injecting gun that allows reading and recording each animal in different stages along their lives, such as vaccinations, treatments of diseases, weightings, deliveries, etc. This recording is of fundamental importance for traceability of animals of a troop.

Traceability, in the processed food sector refers to the capability of tracing food, a fodder, a food producing animal or any substance to be used for being incorporated into them, through all stages of manufacturing, elaboration and distribution that are part of food chain.

Traceability is, therefore, a fundamental tool to guarantee the safety of food as well as the health of people and animals, and thus it is highlighted in the Health Code of the OIE (World Organization of Animal Health).

The use of earrings brought up the need to label and identify cattle. Then, earrings incorporated electronic identification elements by means of readers, which made them more versatile and facilitated controls.

With the use of the first electronic earrings with LF (Low Frequency) technology, there is a need to be close to the animal, since the reader should almost touch the ear of the animal. This necessary closeness is an important practical shortcoming.

Earrings that can be used with the injecting gun of the present invention use RFID technology with UHF frequency which widens the reading scope, which makes possible to take a reading of the animal from a distance of about 4 m with no need to touch the trailer present in the ear of the animal. Also, this technology allows other applications as well as the reading of the animal from some distance.

Particularly, the trigger of the injecting gun according to the present invention is associated to an identification sensor chosen from tactile switches, Hall effect switches, potentiometer and stepper motor.

In a preferred embodiment, the injecting gun of the present invention has tactile switches. By activating said trigger, it presses the switches along the trajectory, said switches being in a series, i.e., they are one after the other.

A first switch activates the RFID module, making the electronic earring to be excited, which sends back the signal received by the reader antenna on the injecting gun. The datum is acknowledged and saved in the gun.

A second switch is activated when an injection is given or when an administration is performed and it ratifies the reader reading, and confirming that the animal identified as "XXXX" has already been vaccinated or treated.

These two switches are associated to a plurality of additional switches, all of which are sequentially linked to administration volumes. Accordingly, the administered volume is known.

All that information is stored in the injecting gun memory and is synchronized by means of a BLUETOOTH® wireless networking module to another auxiliary device kept by the operator in charge of the vaccination or treatment, either a cell phone, a Tablet, a Notebook, or the like, for processing and storage by means of a computer program installed in said devices.

The information of the reading of the earring with treatment is also stored in an SD card (Secure Digital card) in the injecting gun.

This way, the present injecting gun comprising a RFID reading system, which sends a wave and excites a chip inserted in the earring of the animal and implanted in its ear, bouncing with the animal's identification information, is mounted on the animal's injecting gun, which after getting the identification datum for each animal matches it with action of the administering of a corresponding vaccine or drug. That is, if the animal is not vaccinated, the counting and the animal's ID recording is not registered in the list of treated animals. This way, it is checked and certified that the animal was effectively vaccinated or treated, and this makes it different from common systems which only read animals that were supposedly treated, they not having any mechanism to effectively check they were vaccinated or treated.

The injecting gun of the invention is linked through a BLUETOOTH® wireless networking and/or WiFi and/or ZIGBEE® wireless networking and/or GSM wireless connection or wired USB connection to an electronic auxiliary device, preferably a portable device, such as a Smartphone, Tablet, Notebook, or the like. Each animal is identified with a unique earring having a RFID chip inside.

Apart from getting the vaccination or treatment datum, the auxiliary device records other relevant variables, such as the location of the establishment through GPS on the auxiliary device, atmospheric conditions at the time of administration and duration of work in the tube. They are all data which are at the Big Data cloud and are got and recorded by the auxiliary device. Said data are important since they can explain some happenings, such as the vaccination failures or deaths of animals due to a bad handling thereof in case of severe ambient conditions, such as, for example, extremely high temperatures at the moment of performing the work. This way, the correct handling of animals is also controlled by taking this registration of climatic variables.

By having data previously loaded on the system of animals to be treated, it is possible to predict the amount of product to be inoculated, such as the case of antibiotics and anti-parasitic agents where each animal should receive a dose in agreement with its weight. The case of vaccinations where each individual receives the same dose independently of its weight is different.

Therefore, is we have a database with the weights of the animals in the troop, after reading an animal to be treated the system takes the datum of its weight from the database and, based on the recommended dose for the corresponding drug, performs a calculation indicating how much product should be injected to each animal.

For example, when an anti-parasitic agent is used to perform a treatment to a troop with Ivermectin, this is used at a dose of 1 ml/50 kg of living weight, when animals enter the tube they will have a different weight. For example, some will weight 200 kg, others 250 kg and others 300 kg, and the living weight is not easily determined at first sight form each animal, and therefore the dose to be used cannot be determined for each animal. Very usually, an average dose is calculated for the whole troop, and this way some animals will be over-treated, some will be correctly treated and some will be undertreated. This way, when the 200 kg animal enters the system, it will indicate that 4 ml should be used, with the 250 kg animal 5 ml will be used, and with the 300 kg animal 6 ml will be used. This is very important since the bad use of antibiotics and anti-parasitic agents is the main cause of resistance of pathogens and parasites to drugs.

Another use of the injecting gun is as identification aid. The same gun is disassembled, the tube and plunger are removed and it turns into a ID reader for animals to perform Electronic Identification (EID) by means of Radiofrequency (RFID). This is very useful in the case we should identify the animal without passing through the tube, directly on the field, or if we wish to weight the animals and record the kilograms for each one, or also to take other records such as the delivery date, the mating date, changes in the composition of diet, etc.

By using the UHF (Ultra High Frequency) RFID technology in the animal identifier, a greater reading distance may be used, with the benefits from not needing to have the animal locked to read its earring in a manual or closer way. The fact of avoiding lock-ups of animals prevents accidents and stress to them and a very important fact is also that lesions are prevented to the personnel working with animals; it is very common to have lesions on hands for the animal pushing the worker against the tube tables, or head and face bumps with nose breaking due to headbutt of the animal against the worker.

The proposed objectives and the achieved benefits were made with the idea of an injecting gun for the treatment animals with an identification aid which interacts with it acting mechanically when performing a dose administration.

A push button or a trigger of the injecting gun for the treatment of animals with identification aid is pressed when triggering the injecting gun activating a first switch that activates the RFID module that excites the electronic caravan, which sends back the signal which is received by the antenna of the reader on the injecting gun, therefore recognizing the datum which is saved in the injecting gun.

When administering a vaccine or when performing an administration for an anti-parasitic or antibiotic treatment, the second switch is activated validating the reader reading and confirming that the animal identified as "XXXX" has already been vaccinated or treated. The signal is sent to a memory on the injecting gun and is resent through BLUETOOTH® wireless networking and/or WiFi and/or ZIGBEE® and/or GSM wireless connection or wired USB connection to an external electronic device.

Figure 1:
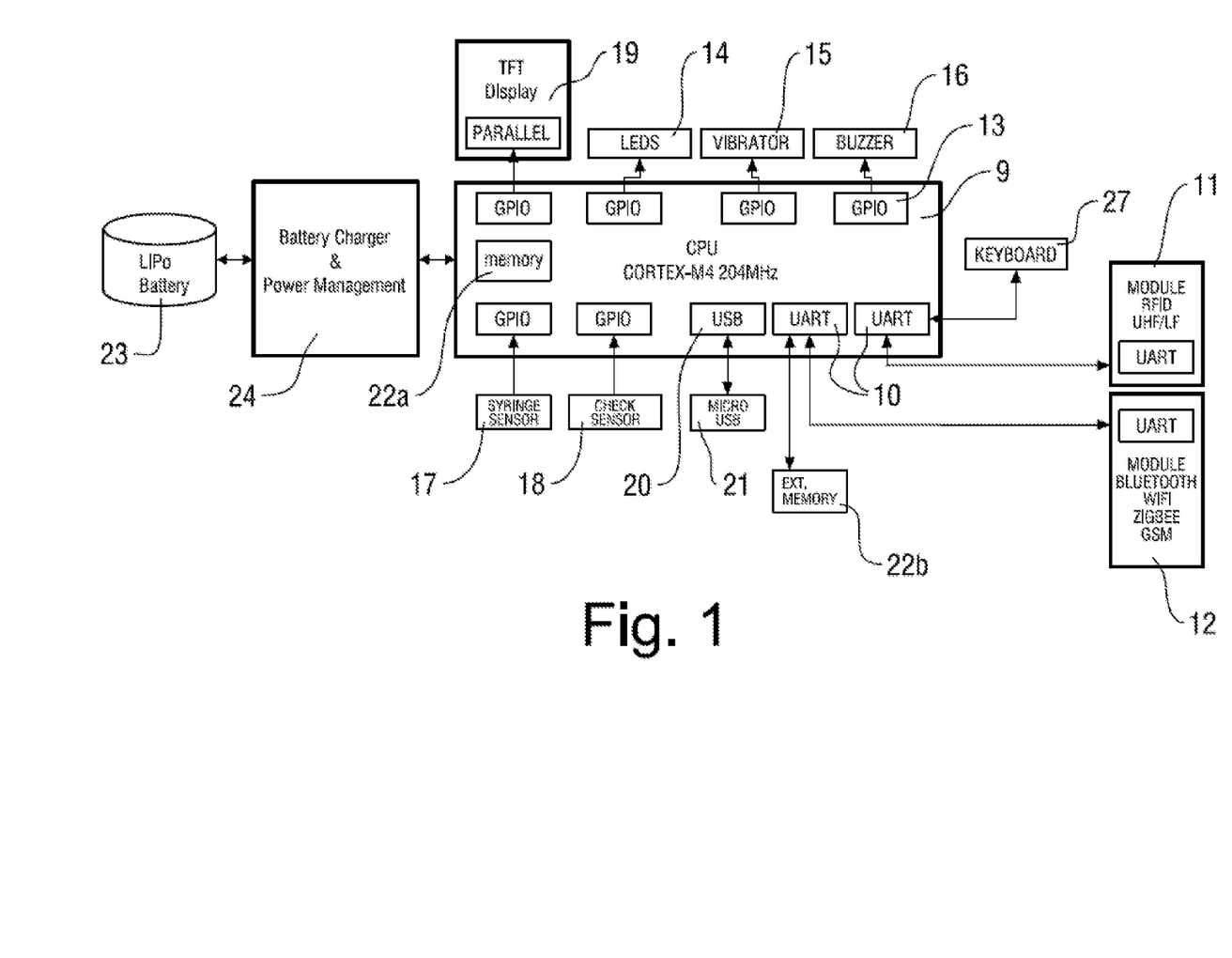
FIG. 1 shows a block diagram of a preferred embodiment of the electronic circuit comprising the CPU of the gun in agreement with the present invention.
Figure 2:
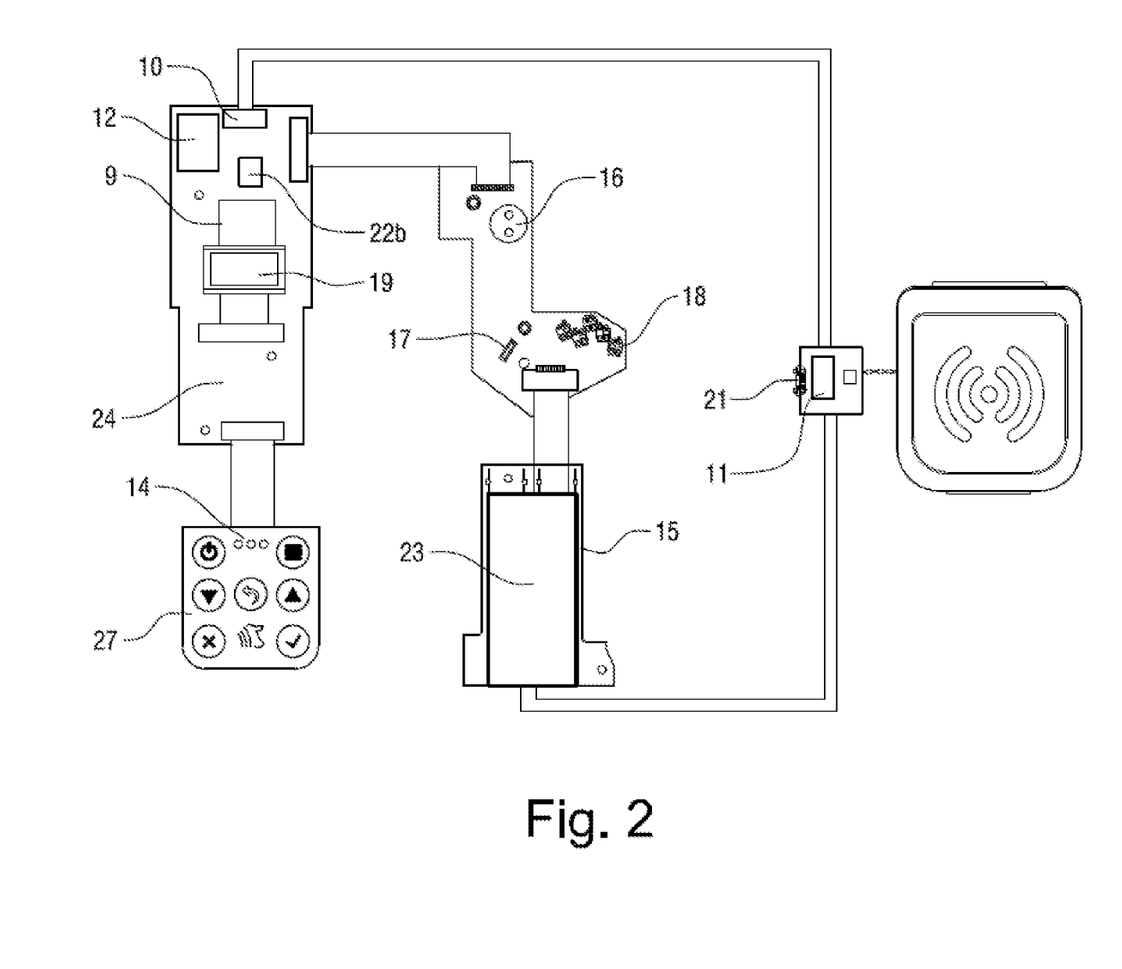
FIG. 2 shows the assembly of elements constituting a preferred embodiment of the injecting gun according with the present invention and the way they are linked.

It is therefore an object of the present invention to achieve an injecting gun (1) for the treatment of animals with an identification aid (2) having a push button (3) (trigger) on the handle (4) comprising a body (5) formed by two main housings (6) connected through their edges which delimitate a free space (7), in which there is an electronic card (8) formed by:

a CPU (Central Processing Unit) (9) which is connected by means of:
   a) a UART (Universal Asynchronous Receiver/Transmitter) module with a multiplicity of connections to:
     i) a RFID (Radio-Frequency Identification) module,
     ii) a wireless connectivity module; and
     iii) a keyboard (27);
   b) a GPIO (General Purpose Input/Output) module with a multiplicity of connections to:
     iii) a plurality of LEDs (Light Emitting Diode) (14),
     iv) a vibrator (15),
     vi) a buzzer (16),
     vii) a syringe sensor (17),
     viii) a verification sensor (18), and ix) one parallel port of a TFT (Thin-Film Transistor) liquid crystal screen (19);

c) one USB (Universal Serial Bus) module (20) with:

x) one micro USB plug (micro USB) (21);

wherein said CPU (9) is connected to a memory (22); and wherein said CPU (9) is connected to a power source (23), which is connected to a battery charger and energy manager (24).

Said CPU is a built-in component and it is selected from Cortex-M0, Cortex-M0+, Cortex-M3, Cortex-M4, Cortex-M7, Cortex-M23, and Cortex-M33 Preferably, said CPU is a built-in component Cortex-M4 204 MHz.

Specifically, the RFID (Radio-Frequency Identification) module is selected from a RFID UHF (Ultra High Frequency) module, a RFID LF (Low Frequency) module, and combinations thereof.

Concretely, the wireless connectivity module is selected from a BLUETOOTH® wireless networking module, a wireless WiFi module, a ZIGBEE® wireless networking module, a wireless GSM (Global System for Mobile communications) module, and combinations thereof.

Particularly, the syringe sensor is a position sensor of the syringe indicating how many ml were injected in a specific moment, recording and validating the administration either of a vaccine or of an injectable treatment.

Preferably, the identification sensor is selected from tactile switches, Hall effect switches, a potentiometer, a stepper motor, and combinations thereof.

For example, when tactile switches are used, the injecting gun (1) comprises a first switch (18a) that activates the RFID (11) module that excites an electronic caravan, which sends back the signal which is received by the antenna (25) of the reader on the injecting gun (1), therefore recognizing the datum which is saved in the injecting gun (1) memory (22). A second switch (18b) is activated when an injection is given thus ratifying the reader reading, and confirming that the identified animal has already been injected. These two tactile switches (18a, 18b) are at the same time associated to corresponding different administration volumes, and at the same time they are coordinated with a plurality of tactile switches (18c-18e) which, as well as both first ones, are all associated to different administration volumes, these tactile switches (18a-18e) being activated one after the other when the trigger (3) of the injecting gun (1) is lowered and raised during the performance of each administration, therefore the RFID module (11) is activated, the performed administration volume is identified, and the performed administration is validated, being these data stored on the memory (22) of the CPU (9).

In a preferred embodiment, the assignments to the tactile switches re as follows: tactile switch (18a)—activation of RFID module/injection volume of 1 ml; tactile switch (18b)—validation of administration/injection volume of 2 ml; tactile switch (18c)—injection volume of 3 ml; tactile switch (18d)—injection volume of 4 ml; e tactile switch (18e)—injection volume of 5 ml.

The injecting gun (1) comprises an internal memory (22a) of the CPU (9), or an external memory (22b), for example, a SD memory card (SD card, Secure Digital card), which is normally complementary and accessory to the internal memory (22a).

As an energy source, at least one Li-Ion (Lithium-Ion) or LiPo (Lithium Polymer) battery (23) may be preferably used. This at least one battery (23) may be recharged by means of a battery charger (24) which is also an energy manager circuit.

The battery charge (23) is performed from an external electromotor source connected to the USB module (20) of the CPU (9) by a micro USB plug (21), which is at the same time connected to the battery charger and energy manager (24) which is connected to the battery (23). When de battery (23) is charged, the energy required by the electronic devices is supplied thereby, at the same time the energy manager circuit of the battery charger (24) disconnects the charge once the battery (23) is charged.

Additionally, the USB module (20) serves for loading and downloading information to/from the injecting gun (1) by means of a suitable connection with the micro USB plug (21). In turn, the BLUETOOTH® wireless networking and/or WiFi and/or ZIGBEE® wireless networking and/or GSM wireless modules (12) allow to connect the injecting gun (1) to different peripheral devices such as cell phones, tablets, computers and/or any device supporting BLUETOOTH® wireless networking and/or WiFi and/or ZIGBEE® wireless networking and/or GSM wireless connectivity, such as scales, identifiers, mechanical fixes, Hubs, switches, routers, among others. All treatments, animals and identifiers are stored on the memory (22a, 22b) of the injecting gun, allowing the user to download the information through the USB port (21) or the BLUETOOTH® wireless networking and/or WiFi and/or ZIGBEE® wireless networking and/or GSM wireless module (12) to a mobile useful application in order to process it or as a text file.

The CPU (9) has a computer program installed with instructions that allow the injecting gun (1) providing the user with all the supplies and facilities needed to perform the tasks related with the treatment, identification and traceability of animal as described herein.

Figure 3:
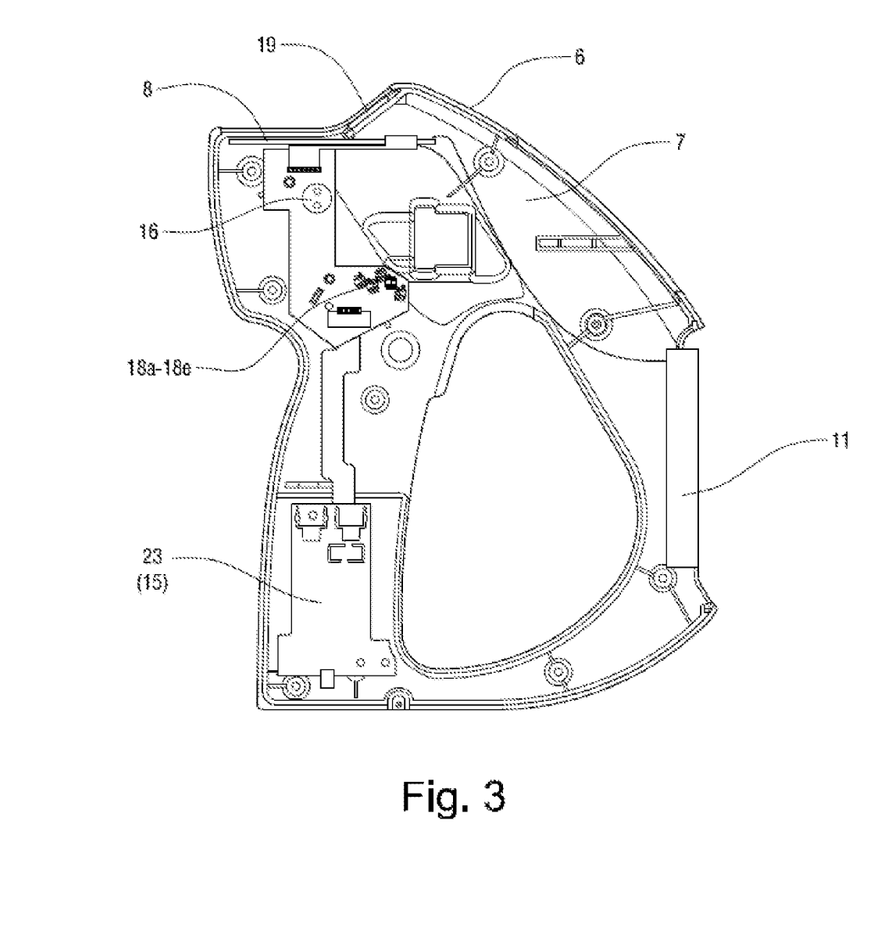
FIG. 3 shows a cross-section of the injecting gun handle according to the present invention with the portion used for injecting animals disassembled, thus showing the arrangement of the constitutive elements shown in FIG. 2. Without the injecting portion, the gun of the invention may be used as an identification device.
Figure 4:
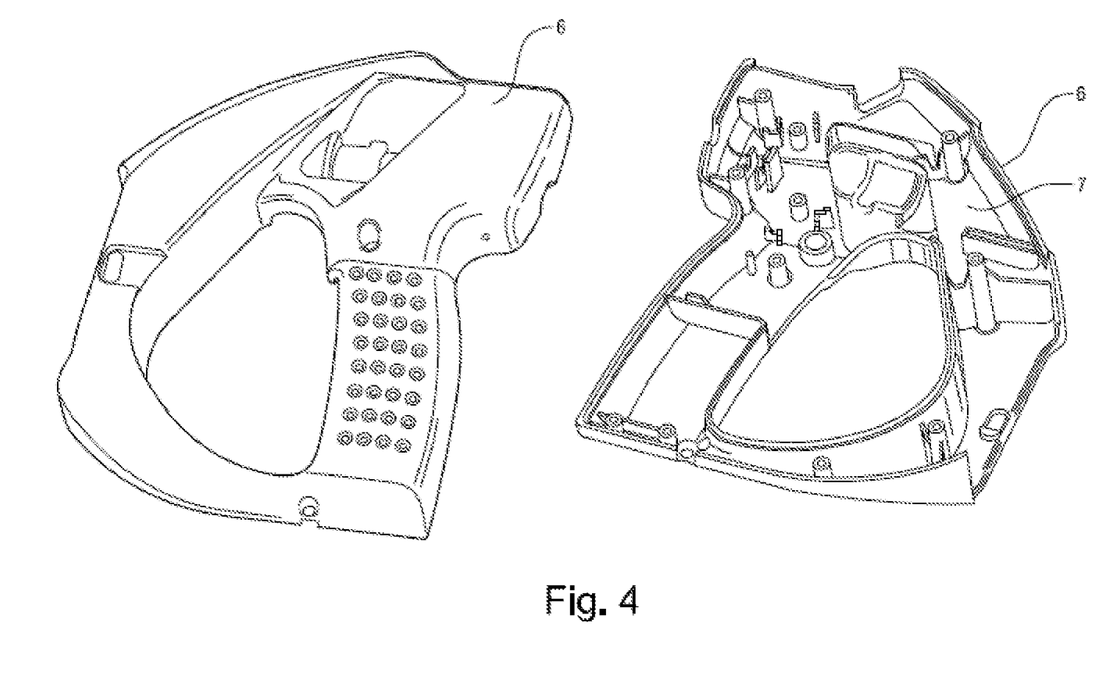
FIG. 4 shows both left and right halves of the handle according to a preferred embodiment of the invention which is shown as a cross-section in FIG. 3, without the constitutive elements assembled.
Figures 5, 6:
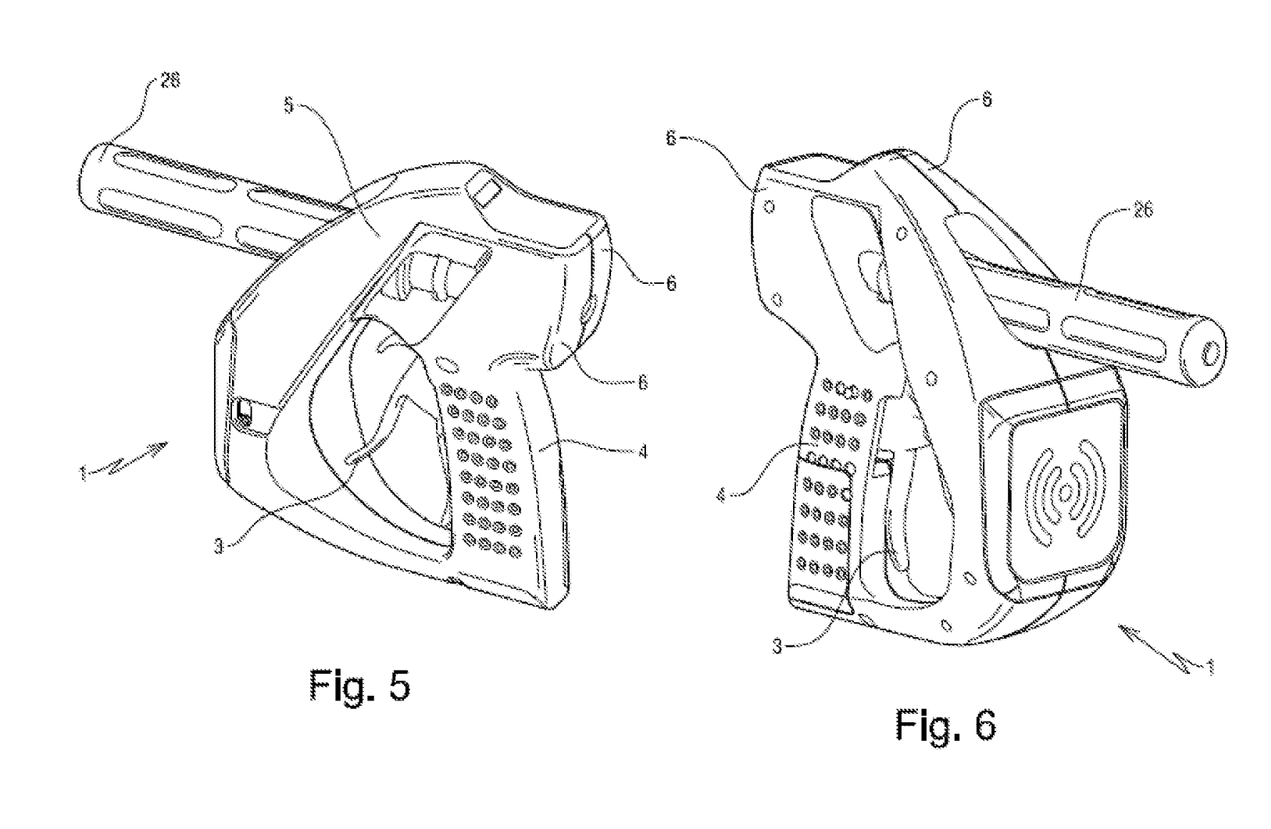
FIG. 5 shows a top, lateral-rear perspective view of the injecting gun according to a preferred embodiment of the present invention, wherein the trigger is deployed.
FIG. 6 shows a top, lateral-front perspective view of the injecting gun according to a preferred embodiment of the present invention, wherein the trigger is drawn back.

Likewise, by disassembling the portion (26) of the injecting gun (1) which is used to inject animals, the injecting gun (1) of the invention turns into an identification device.

It is also an object of this invention to increase the quality standards as regards service and professionalism of this sector, giving the chance to have accurate information by the use of the injecting gun according to the present invention, and thus increasing the welfare of the animals by avoiding excessive or inappropriate movements of the cattle, as it is usually done in some cases when moving them from one farmyard to another, one animal after the other, to identify them and eventually to treat them by using the prior art technologies,

The invention claimed is:

1. An injecting gun for the treatment of animals with an identification aid having a push button on a handle comprising a body formed by two main housings connected through their edges which delimit a free space, in which there is an electronic card formed by:

a CPU (Central Processing Unit) which is connected to:

a) an UART (Universal Asynchronous Receiver/Transmitter) module with a multiplicity of connections connected to:

i) a RFID (Radio-Frequency Identification) module, ii) a wireless connectivity module; and iii) a keyboard;

b) a GPIO (General Purpose Input/Output) module with a multiplicity of connections connected to:

iii) a plurality of LEDs (Light Emitting Diodes), iv) a vibrator, vi) a buzzer, vii) a syringe sensor, viii) a identification sensor comprising a first tactile switch which activates the RFID module which excites an electronic earring, which sends a signal back which is received by a reader antenna at the injecting gun thereby recognizing data saved in a memory of the injecting gun; and a second tactile switch which is activated when giving an injection and matches a reader reading, confirming that an animal has been injected, said tactile switches activated by the push button, and ix) one parallel port of a TFT (Thin-Film Transistor) liquid crystal screen;

c) one USB (Universal Serial Bus) module with:

x) one micro USB plug (micro USB);

wherein said CPU is connected to the memory;

wherein said CPU is connected to a power source, which is connected to a battery charger and an energy manager; and wherein the first and second tactile switches are associated with respective different application volumes, wherein said first and second tactile switches are coordinated with a plurality of additional tactile switches which are associated with different application volumes, and wherein said tactile switches are activated one after the other when the push button of the injecting gun is lowered and raised during each administration of an injection.

2. The injecting gun according to claim 1, wherein said CPU is a built-in component selected from the group consisting of Cortex-M0, Cortex-M0+, Cortex-M3, Cortex-M4, Cortex-M7, Cortex-M23, and Cortex-M33.

3. The injecting gun according to claim 2, wherein said CPU is a built-in Cortex-M4 204 MHz component.

4. The injecting gun according to claim 1, wherein the RFID (Radio-Frequency Identification) module is selected from the group consisting of a RFID UHF (Ultra High Frequency) module, a RFID LF (Low Frequency) module, and combinations thereof.

5. The injecting gun according to claim 1, wherein the wireless connectivity module is a device that supports BLUETOOTH® wireless networking and/or WiFi and/or ZIGBEE® wireless networking and/or GSM (Global System for Mobile communications) wireless connectivity or combinations thereof.

6. The injecting gun according to claim 1, wherein the first tactile switch is associated with activation of the RFID module and with an injection volume of 1 ml; the second tactile switch is associated with validation of administration and with an injection volume of 2 ml; a third tactile switch is associated with an injection volume of 3 ml; a fourth tactile switch is associated with an injection volume of 4 ml; and a fifth tactile switch is associated with an injection volume of 5 ml.

7. The injecting gun according to claim 1, wherein by lowering and raising the push button of the injecting gun when performing each administration, the RFID module is activated, the volume of each performed administration is identified and the performed administration is validated, these data being saved on the memory associated with the CPU.

8. The injecting gun according to claim 1, wherein said memory is selected from the group consisting of an internal memory of the CPU, an external memory and a combination thereof.

9. The injecting gun according to claim 8, wherein said external memory is a SD memory card (SD card, Secure Digital card).

10. The injecting gun according to claim 1, wherein the power source comprises a Li-Ion (Lithium-Ion) battery or a LiPo (Lithium-Polymer) battery, adapted to be recharged by the battery charger associated with a circuit of the energy manager.

11. The injecting gun according to claim 1, wherein the power source is charged through the USB module of the CPU from an electromotor source.

12. The injecting gun according to claim 1, wherein information is loaded and/or downloaded to and/or from the injecting gun to and/or from a peripheral device.

13. The injecting gun according to claim 12, wherein the peripheral device is a cell phone, a tablet, a computer, a scale, an identifier, a mechanic fix, a hub, a switch, a router, or a device that supports BLUETOOTH® wireless networking and/or WiFi and/or ZIGBEE® wireless networking and/or GSM wireless connectivity.

14. The injecting gun according to claim 12, wherein the information is loaded and/or downloaded to and/or from the peripheral device through the wireless connectivity module.

15. An identification device comprising the injecting gun according to claim 1 further comprising a portion used for injecting animals, wherein the portion used for injecting animals can be dissembled.

\* \* \* \* \*